(12) United States Patent
Geum et al.

(10) Patent No.: US 11,980,649 B2
(45) Date of Patent: May 14, 2024

(54) **COMPOSITION FOR THE PREVENTION OR TREATMENT OF RESPIRATORY DISEASES CAUSED BY FINE DUST COMPRISING *AGASTACHE RUGOSA* AND LICORICE EXTRACT**

(71) Applicants: Cosmax NBT, Inc., Seoul (KR); Cosmax NS, Inc., Seoul (KR)

(72) Inventors: Jeong Ho Geum, Seoul (KR); Hye Rim Kim, Seoul (KR); Jin Hak Kim, Seoul (KR); Su Young Choi, Seoul (KR)

(73) Assignees: Cosmax NBT, Inc., Seoul (KR); Cosmax NS. Inc., Seoul (KR)

( * ) Notice: Subject to any disclaimer, the term of this patent is extended or adjusted under 35 U.S.C. 154(b) by 0 days.

(21) Appl. No.: 17/257,529

(22) PCT Filed: May 21, 2020

(86) PCT No.: PCT/KR2020/006617
§ 371 (c)(1),
(2) Date: Dec. 31, 2020

(87) PCT Pub. No.: WO2021/167168
PCT Pub. Date: Aug. 26, 2021

(65) Prior Publication Data
US 2023/0210932 A1    Jul. 6, 2023

(30) Foreign Application Priority Data
Feb. 19, 2020  (KR) .................. 10-2020-0020369

(51) Int. Cl.
| | | |
|---|---|---|
| *A61K 36/00* | (2006.01) | |
| *A23L 33/105* | (2016.01) | |
| *A61K 36/484* | (2006.01) | |
| *A61K 36/532* | (2006.01) | |

(52) U.S. Cl.
CPC .......... *A61K 36/532* (2013.01); *A23L 33/105* (2016.08); *A61K 36/484* (2013.01)

(58) Field of Classification Search
CPC ........................ A61K 36/484; A61K 36/532
See application file for complete search history.

(56) References Cited

U.S. PATENT DOCUMENTS

| | | |
|---|---|---|
| 11,160,840 B2 | 12/2021 | Hwang et al. |
| 2020/0009208 A1 | 1/2020 | Hwang et al. |
| 2021/0401916 A1 | 12/2021 | Hwang et al. |
| 2022/0080018 A1 | 3/2022 | Jang et al. |

FOREIGN PATENT DOCUMENTS

| | | | | |
|---|---|---|---|---|
| CN | 101564460 | | 10/2009 | |
| CN | 102132916 A | * | 7/2011 | |
| CN | 106070838 A | * | 11/2016 | ............. A23F 3/163 |
| KR | 10-2002-0013134 | | 2/2002 | |
| KR | 10-2003-0007243 | | 1/2003 | |
| KR | 10-2011-0051163 | | 5/2011 | |
| KR | 10-2013-0111050 | | 10/2013 | |
| KR | 10-2013-0133610 | | 12/2013 | |

OTHER PUBLICATIONS

Zheng et al, Terpenes and phenolic compounds from agastache rugosa and their inhibitory effect on the release of β-hexosaminidase inZheng et al, Terpenes and phenolic compounds from agastache rugosa and their inhibitory ef RBL-2H3 cells. Planta Medica, (Jul. 2013) vol. 79, No. 10. Abs: PN93 (Year: 2013).*
Wang, Glycyrrhizic acid as the antiviral component of Glycyrrhiza uralensis Fisch. against coxsackievirus A16 and enterovirus 71 of hand foot and mouth disease. Journal of ethnopharmacology, (May 2, 2013) vol. 147, No. 1, pp. 114-121 (Year: 2013).*
U.S. Appl. No. 17/935,043, filed Sep. 23, 2022, by Geum et al. (Copy not submitted herewith pursuant to the waiver of 37 C.F.R. § 1.98(a)(2)(iii) issued by the Office on Sep. 21, 2004).
CIP (cataloguing in publication) data Xiu Zhen color atlas of Chinese herbal medicine, and English translation/Edited by Chen Zhipeng et al.—Changsha:Hunan Science and Technology Press, 2016.10 ISBN 978-7-5357-9046-0.

* cited by examiner

*Primary Examiner* — Qiuwen Mi
(74) *Attorney, Agent, or Firm* — Morrison & Foerster LLP

(57) ABSTRACT

The *Agastache rugosa* and licorice complex mixture of the present invention has the synergy effects for the efficacies of reducing cough through inhibition of TRPV1 activity, reducing lung inflammation through inhibition of CXCR1 and CXCR2 activities and GR-1+CD11b+ cell ratio reduction, and suppressing sputum production through inhibition of MUC5AC activity and therefore it can be widely utilized as a composition for the prevention or treatment of respiratory diseases.

3 Claims, 5 Drawing Sheets

Specification includes a Sequence Listing.

```
                              SEQUENCE LISTING

<160> NUMBER OF SEQ ID NOS: 9

<210> SEQ ID NO 1
<211> LENGTH: 21
<212> TYPE: DNA
<213> ORGANISM: Artificial
<220> FEATURE:
<223> OTHER INFORMATION: CXCR1_F

<400> SEQUENCE: 1
aatctgttgt ggcttcaccc a                                          21

<210> SEQ ID NO 2
<211> LENGTH: 21
<212> TYPE: DNA
<213> ORGANISM: Artificial
<220> FEATURE:
<223> OTHER INFORMATION: CXCR1_R

<400> SEQUENCE: 2
gctatcttcc gccaggcata t                                          21

<210> SEQ ID NO 3
<211> LENGTH: 24
<212> TYPE: DNA
<213> ORGANISM: Artificial
<220> FEATURE:
<223> OTHER INFORMATION: CXCR2_F

<400> SEQUENCE: 3
agcaaacacc tctactaccc tcta                                       24

<210> SEQ ID NO 4
<211> LENGTH: 23
<212> TYPE: DNA
<213> ORGANISM: Artificial
<220> FEATURE:
<223> OTHER INFORMATION: CXCR2_R

<400> SEQUENCE: 4
gggctgcatc aattcaaata cca                                        23

<210> SEQ ID NO 5
<211> LENGTH: 19
<212> TYPE: DNA
<213> ORGANISM: Artificial
<220> FEATURE:
<223> OTHER INFORMATION: GAPDH_F

<400> SEQUENCE: 5
tgaagcaggc atctgaggg                                             19

<210> SEQ ID NO 6
<211> LENGTH: 20
<212> TYPE: DNA
<213> ORGANISM: Artificial
<220> FEATURE:
<223> OTHER INFORMATION: GAPDH_R

<400> SEQUENCE: 6
cgaaggtgga agagtgggag                                            20
```

```
<210> SEQ ID NO 7
<211> LENGTH: 24
<212> TYPE: DNA
<213> ORGANISM: Artificial
<220> FEATURE:
<223> OTHER INFORMATION: MUC5AC_F

<400> SEQUENCE: 7
agaatatctt tcaggacccc tgct                                              24

<210> SEQ ID NO 8
<211> LENGTH: 23
<212> TYPE: DNA
<213> ORGANISM: Artificial
<220> FEATURE:
<223> OTHER INFORMATION: MUC5AC_R

<400> SEQUENCE: 8
acaccagtgc tgagcatact ttt                                               23

<210> SEQ ID NO 9
<211> LENGTH: 26
<212> TYPE: DNA
<213> ORGANISM: Artificial
<220> FEATURE:
<223> OTHER INFORMATION: GAPDH-VIC probe

<400> SEQUENCE: 9
catgttccag tatgactcca ctcacg                                            26
```

COMPOSITION FOR THE PREVENTION OR TREATMENT OF RESPIRATORY DISEASES CAUSED BY FINE DUST COMPRISING *AGASTACHE RUGOSA* AND LICORICE EXTRACT

CROSS REFERENCE TO RELATED APPLICATIONS

This application is a national stage application under 35 U.S.C. § 371 of International Application No. PCT/KR2020/006617, filed internationally on May 21, 2020, which claims priority to and the benefit of Korean Patent Application No. 10-2020-0020369, filed on Feb. 19, 2020, the disclosures of which are incorporated herein by reference in their entirety.

INCORPORATION BY REFERENCE OF SEQUENCE LISTING

The present application is being filed along with a Sequence Listing in electronic format. The Sequence Listing is provided as a file entitled 717572003400SeqList.txt, created Dec. 30, 2020, which is 1.95 kilobytes in size. The information in the electronic format of the Sequence Listing is incorporated by reference in its entirety.

TECHNICAL FIELD

The present invention relates to a composition for the prevention or treatment of respiratory diseases containing an *Agastache rugosa* and licorice extract as an active ingredient, and more specifically, the present invention relates to a composition for the prevention or treatment of respiratory diseases caused by fine dust containing an extract, in which *Agastache rugosa* and licorice are mixed at a weight ratio of 1:1 to 6:1, as an active ingredient.

BACKGROUND ART

Due to the recent development of the industry and economy, the occurrence of respiratory diseases is rapidly increasing due to environmental population and changes in diet. Increased mortality and prevalence due to air pollution is one of the major risks for human health, and the World Health Organization also reported that about 3 million people die each year due to air pollution (approximately 5% of the total deaths), and these effects on the human body are known to be mainly due to fine dust generated during the combustion of fossil fuels.

Fine dust refers to particulate matter less than 10 μm in diameter (PM10) among the total suspended particles in the air, and it is known to cause diseases such as respiratory diseases, cardiovascular diseases, and the like, and it is also associated with increased mortality. Most of the fine dust is generated by the combustion of fossil fuels, and as it is not filtered by the mucous membrane and cilia of the nose and airways, it penetrates into the alveoli and bronchi to inhibit lung function. Long-term exposure to fine dust causes not only respiratory diseases such as chronic obstructive pulmonary disease (COPD), bronchitis, pneumonia, tuberculosis, lung cancer, pulmonary fibrosis, chronic lung diseases, respiratory distress syndrome, upper respiratory tract infection, and the like, but also various diseases such as cardiovascular diseases, skin diseases, and the like.

When fine dust enters through the respirator tract, it is difficult to discharge, and there is no way to forcefully discharge it. Thus, since it is not exactly known when and what problem will happen with such damage, there is an urgent need for a new therapeutic agent that can prevent, alleviate, treat, or ameliorate damages of the airway and lung induced by fine dust, which is capable of treating respiratory diseases induced thereby.

As such, in the present invention, as a result of diligently making efforts to develop an effective therapeutic agent for respiratory diseases caused by fine dust, it was confirmed that the efficacy of an *Agastache rugosa* and licorice extract was maximized at a specific mixing ratio. In particular, the present invention was completed by confirming that lung inflammation, cough, and sputum that characterize the infiltration of neutrophils, which is a respiratory symptom caused by fine dust, were effectively suppressed.

DISCLOSURE

Technical Problem

An object of the present invention is to provide a pharmaceutical composition for preventing or treating a respiratory disease containing an *Agastache rugosa* and licorice extract as an active ingredient.

Another object of the present invention is to provide a health functional food composition for preventing or treating a respiratory disease containing an *Agastache rugosa* and licorice extract as an active ingredient.

Technical Solution

In order to attain the above-described objects, the present invention provides a pharmaceutical composition for preventing or treating a respiratory disease containing an *Agastache rugosa* and licorice extract as an active ingredient.

In addition, the present invention provides a health functional food composition for preventing or ameliorating a respiratory disease containing an *Agastache rugosa* and licorice extract as an active ingredient.

According to a preferred exemplary embodiment of the present invention, the respiratory disease may be induced by inhalation of fine dust and may be one or more selected from the group consisting of respiratory inflammatory pulmonary disease, chronic obstructive pulmonary disease (COPD), sinusitis, allergic rhinitis, lower respiratory tract infection, acute and chronic bronchitis, emphysema, pneumonia, bronchial asthma, bronchiectasis, pulmonary tuberculosis sequelae, acute respiratory distress syndrome, and pulmonary fibrosis.

According to another preferred exemplary embodiment of the present invention, the *Agastache rugosa* and licorice extract may be a mixture of an *Agastache rugosa* extract and a licorice extract, or an *Agastache rugosa* and licorice complex extract.

According to another preferred exemplary embodiment of the present invention, the *Agastache rugosa* and licorice extract may be mixed with *Agastache rugosa* and licorice at a weight ratio of 1:1 to 6:1.

According to still another preferred exemplary embodiment of the present invention, the *Agastache rugosa* and licorice extract may be extracted using one or more solvents selected from the group consisting of water, ethanol, alcohol having a carbon number of 1 to 4, hexane, and ethyl acetate.

According to still another preferred exemplary embodiment of the present invention, the *Agastache rugosa* and licorice complex extract may reduce cough through inhibition of TRPV1 activity.

According to still another preferred exemplary embodiment of the present invention, the *Agastache rugosa* and licorice complex extract may suppress inflammation in the lungs through inhibition of CXCR1 or CXCR2 activity, or GR-1+CD11 b+ cell ratio reduction.

According to still another preferred exemplary embodiment of the present invention, the *Agastache rugosa* and licorice complex extract may suppress sputum production through inhibition of MUC5AC activity.

Advantageous Effects

The *Agastache rugosa* and licorice extract of the present invention has efficacies of reducing cough through inhibition of TRPV1 activity, reducing lung inflammation through inhibition of CXCR1 and CXCR2 activities and GR-1+CD11b+ cell ratio reduction, and suppressing sputum production through inhibition of MUC5AC activity. In particular, since it is confirmed that the efficacy of the complex mixture of *Agastache rugosa* and licorice is maximized at a specific mixing ratio, it can be widely utilized as a composition for the prevention or treatment of respiratory diseases caused by fine dust.

MODES OF THE INVENTION

Hereinafter, the present invention will be described in detail.

In one aspect, the present invention relates to a pharmaceutical composition for preventing or treating a respiratory disease containing an *Agastache rugosa* and licorice extract as an active ingredient.

The respiratory disease may be induced by inhalation of fine dust and may be one or more selected from the group consisting of respiratory inflammatory pulmonary disease, chronic obstructive pulmonary disease (COPD), sinusitis, allergic rhinitis, lower respiratory tract infection, acute and chronic bronchitis, pneumonia, bronchial asthma, bronchiectasis, emphysema, pulmonary tuberculosis sequelae, acute respiratory distress syndrome, and pulmonary fibrosis.

The *Agastache rugosa* and licorice extract may be mixed with *Agastache rugosa* and licorice at a weight ratio of 1:1 to 6:1, and preferably, at a weight ratio of 4:1. In addition, while *Agastache rugosa* and licorice were mixed together to extract (a complex extract) in the present invention, an *Agastache rugosa* extract and a licorice extract may be prepared separately and then used by mixing depending on the purpose.

The pharmaceutical composition for preventing or treating a respiratory disease according to the present invention may further include a natural extract that has an effect of preventing, treating, or ameliorating respiratory diseases, a fraction thereof, or a compound thereof, in addition to *Agastache rugosa* and licorice.

As a solvent for extracting the *Agastache rugosa* or licorice, water or an organic solvent such as ethanol or alcohol having a carbon number of 1 to 4, hexane, ethyl acetate, and the like may be used alone in combination. Preferably, the *Agastache rugosa* and licorice extract of the present invention may be extracted by ethanol.

In a specific embodiment of the present invention, an *Agastache rugosa* and licorice extract was prepared using ethanol such that the mixing ratio of *Agastache rugosa* to licorice was 1:1 to 6:1, respectively, and as comparative examples, an *Agastache rugosa*-only extract and a licorice-only extract were prepared.

Figure 1:
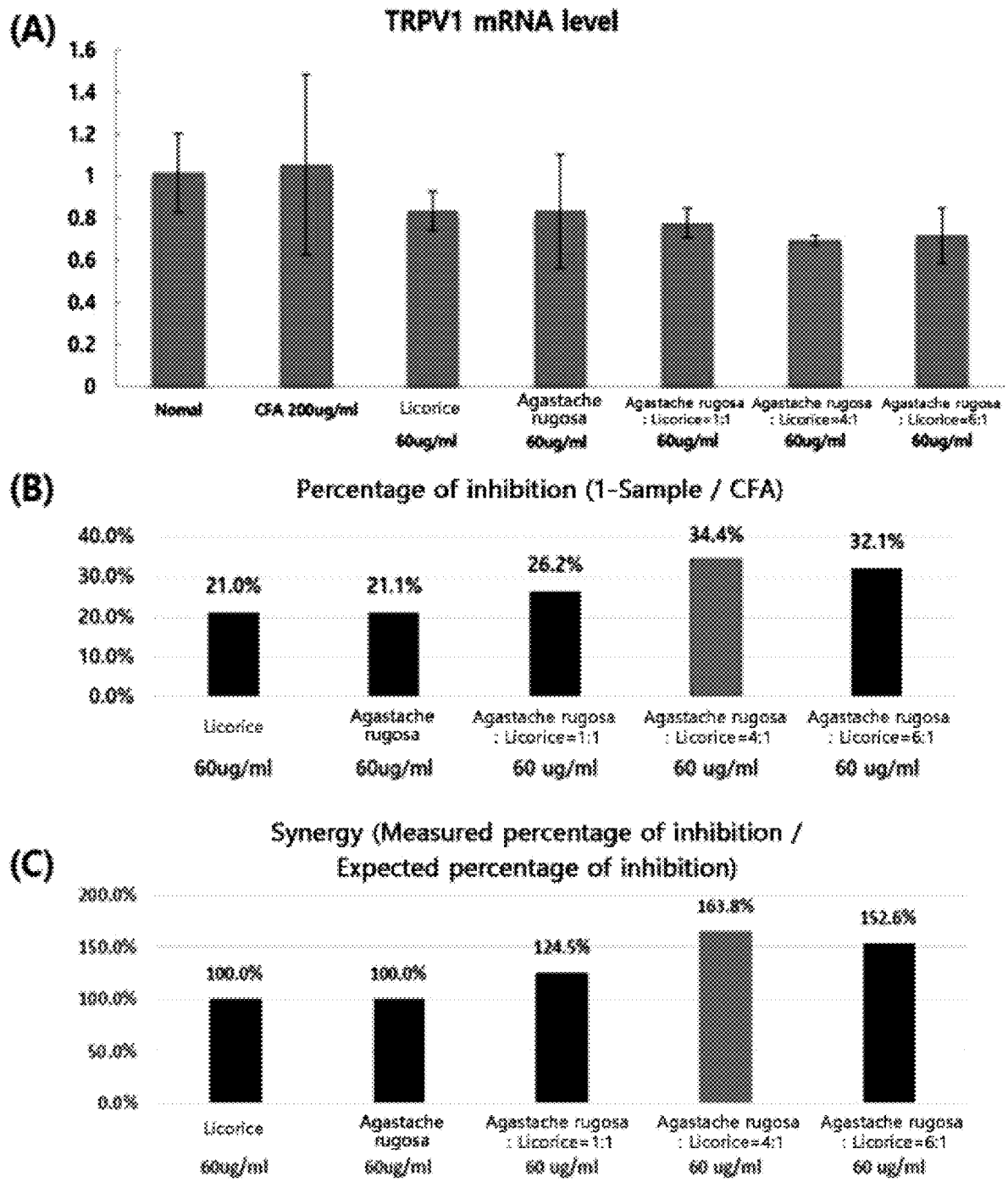
FIG. 1 is a set of data showing the degree of inhibition of TRPV1 activity according to the mixing ratios of licorice and *Agastache rugosa*. (A) is data showing the percentage of inhibition of TRPV1 mRNA expression, (B) is data showing the percentage of inhibition according to the treatment of each extract compared to CFA treatment groups, and (C) is data confirming the synergy effect according to the mixing ratios of licorice and *Agastache rugosa*.

In another specific embodiment of the present invention, the efficacy of an *Agastache rugosa* and licorice extract on preventing or ameliorating various respiratory symptoms caused by fine dust was confirmed. First, as a result of confirming the expression level of TRVP-1 known as a cough receptor, it was confirmed that the TRPV1 inhibitory activity was high in the treatment groups of *Agastache rugosa* and licorice complex extracts (Experimental Examples 1 to 3), compared to an *Agastache rugosa*-only extract (Comparative Example 1) and a licorice-only extract (Comparative Example 2). In particular, it was confirmed that the efficacy of suppressing cough was maximized in a complex extract in which *Agastache rugosa* and licorice were mixed at a ratio of 4:1 (FIG. 1).

In still another specific embodiment of the present invention, as a result of confirming the expression levels of CXCR1 and CXCR2 which are lung inflammatory factors in order to confirm the efficacy of ameliorating the infiltration of neutrophils, which is a characteristic of respiratory diseases caused by fine dust, it was confirmed that the CXCR1 and CXCR2 inhibitory activities were high in the treatment groups of the *Agastache rugosa* and licorice complex extracts (Experimental Groups 1 to 3), compared to the

Figure 2:
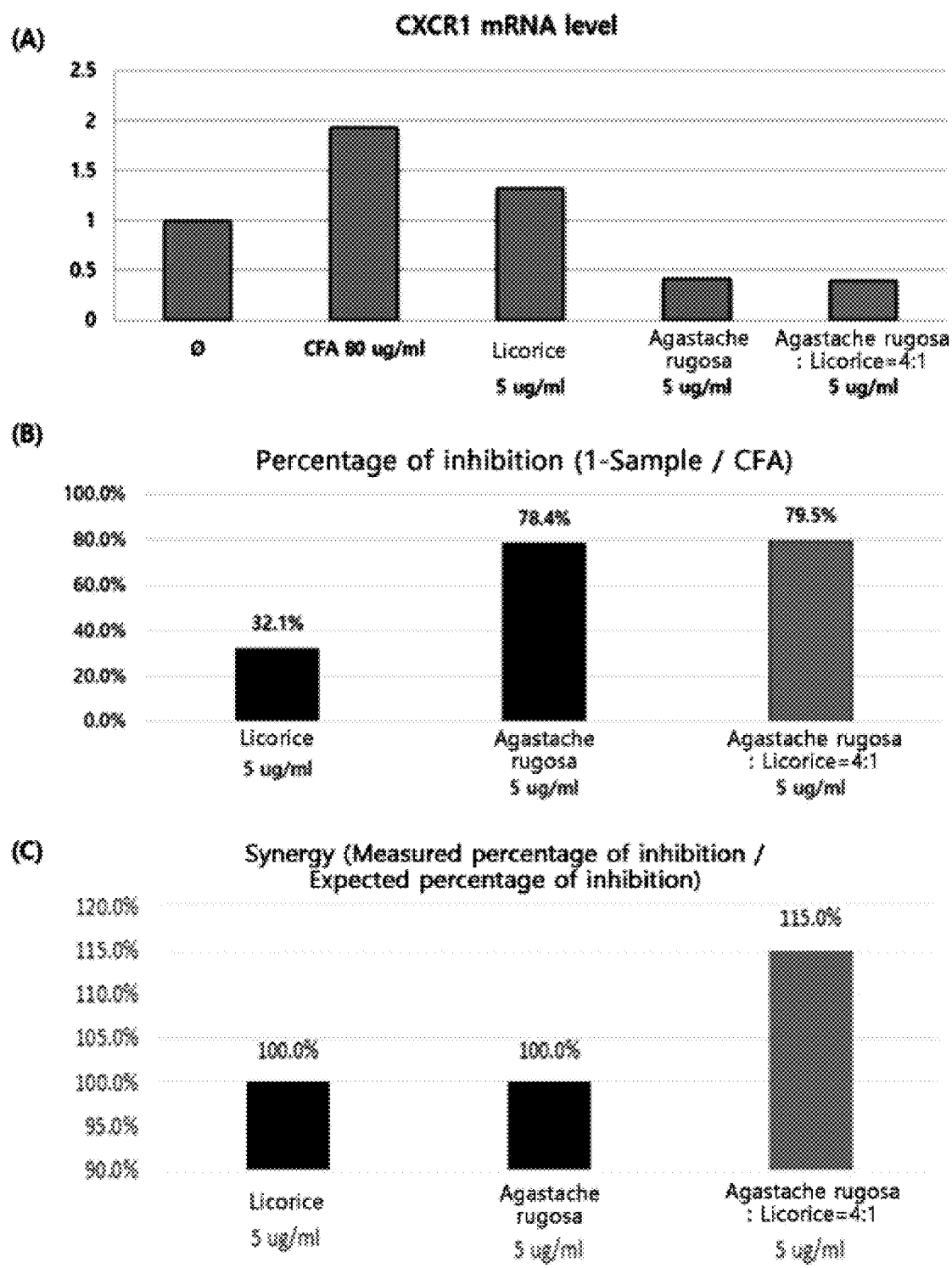
FIG. 2 is a set of data showing the degree of inhibition of CXCR1 activity according to the mixing ratios of licorice and *Agastache rugosa*. (A) is data showing the percentage of inhibition of CXCR1 mRNA expression, (B) is data showing the percentage of inhibition according to the treatment of each extract compared to CFA treatment groups, and (C) is data confirming the synergy effect according to the mixing ratios of licorice and *Agastache rugosa*.
Figure 3:
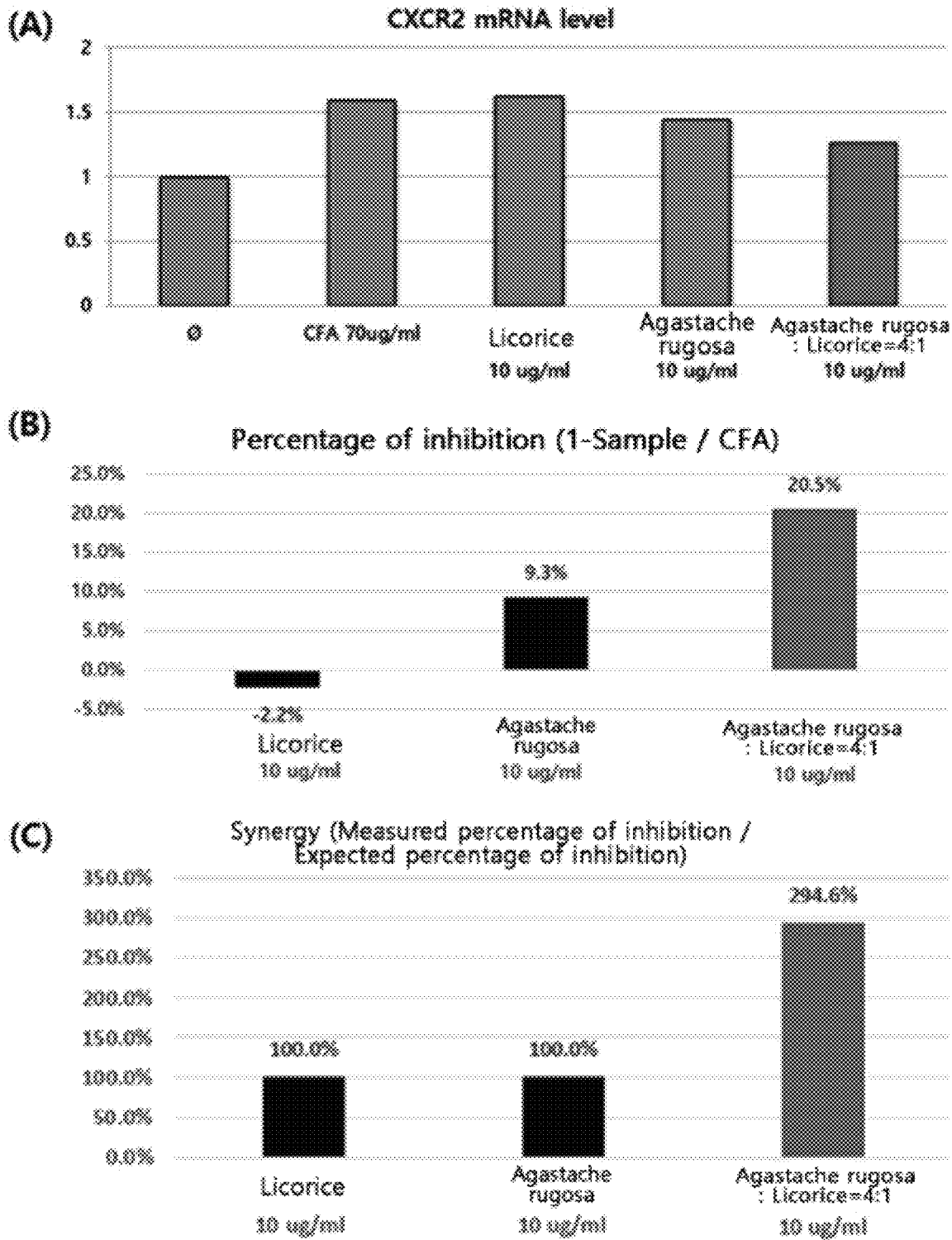
FIG. 3 is a set of data showing the degree of inhibition of CXCR2 activity according to the mixing ratios of licorice and *Agastache rugosa*. (A) is data showing the percentage of inhibition of CXCR2 mRNA expression, (B) is data showing the percentage of inhibition according to the treatment of each extract compared to CFA treatment groups, and (C) is data confirming the synergy effect according to the mixing ratios of licorice and *Agastache rugosa*.

*Agastache rugosa*-only extract (Comparative Example 1) and the licorice-only extract (Comparative Example 2) (FIG. 2 and FIG. 3).

Figure 4:
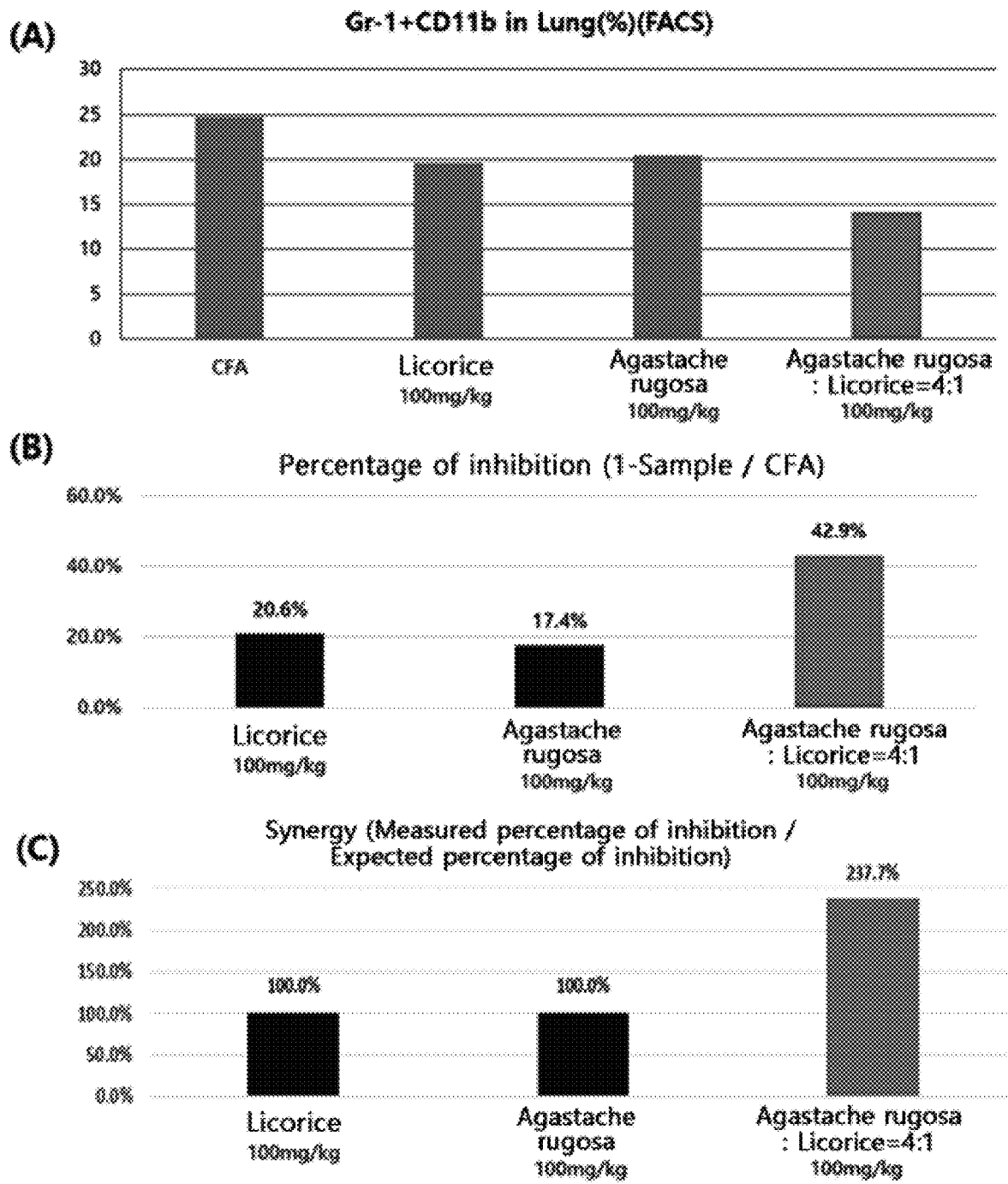
FIG. 4 is a set of data showing the degree of inhibition of GR-1+CD11b+ cell activity according to the mixing ratios of licorice and *Agastache rugosa*. (A) is data showing the percentage of inhibition of GR-1+CD11b+ cells, (B) is data showing the percentage of inhibition according to the treatment of each extract compared to CFA treatment groups, and (C) is data confirming the synergy effect according to the mixing ratios of licorice and *Agastache rugosa*.

In addition, as a result of confirming the Gr-1+CD11b cell ratio in lung tissue in order to confirm that the *Agastache rugosa* and licorice extract suppressed lung inflammation in vivo, it was confirmed that low CD11b+/Gr-1+ leukocyte ratios were shown in the treatment groups of the *Agastache rugosa* and licorice complex extracts (Experimental Groups 1 to 3), compared to the *Agastache rugosa*-only extract (Comparative Example 1) and the licorice-only extract (Comparative Example 2)(FIG. 4).

That is, since it was confirmed that the *Agastache rugosa* and licorice extract not only inhibited CXCR1 and CXCR2 expressions, but also significantly reduced the ratio of CD11b+/Gr-1+ cells (neutrophils) in the lung tissue, it was confirmed to have efficacy for ameliorating the infiltration of neutrophils, which is a characteristic of respiratory diseases caused by fine dust.

Figure 5:
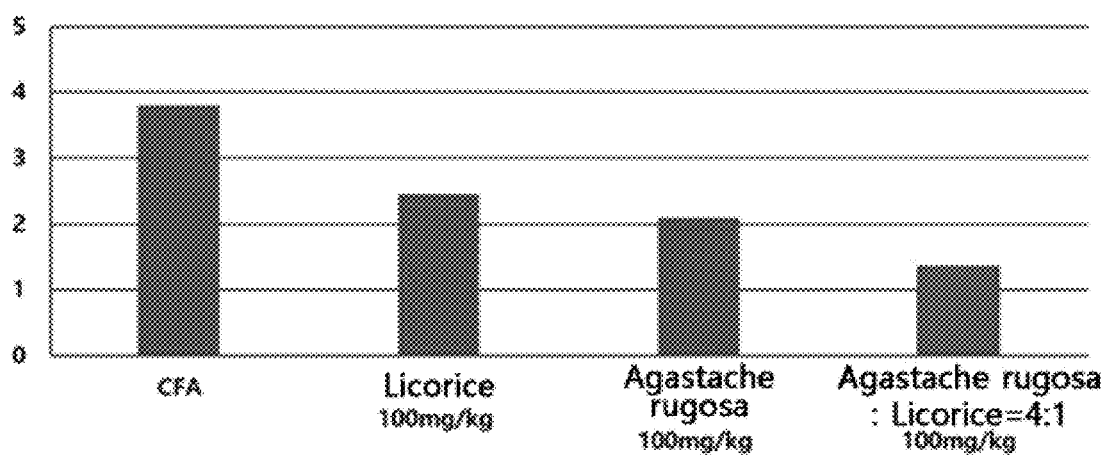
FIG. 5 is a set of data showing the degree of inhibition of MUC5AC activity according to the mixing ratios of licorice and *Agastache rugosa*. (A) is data showing the percentage of inhibition of MUC5AC mRNA expression, (B) is data showing the percentage of inhibition according to the treatment of each extract compared to CFA treatment groups, and (C) is data confirming the synergy effect according to the mixing ratios of licorice and *Agastache rugosa*.
Figure 5:
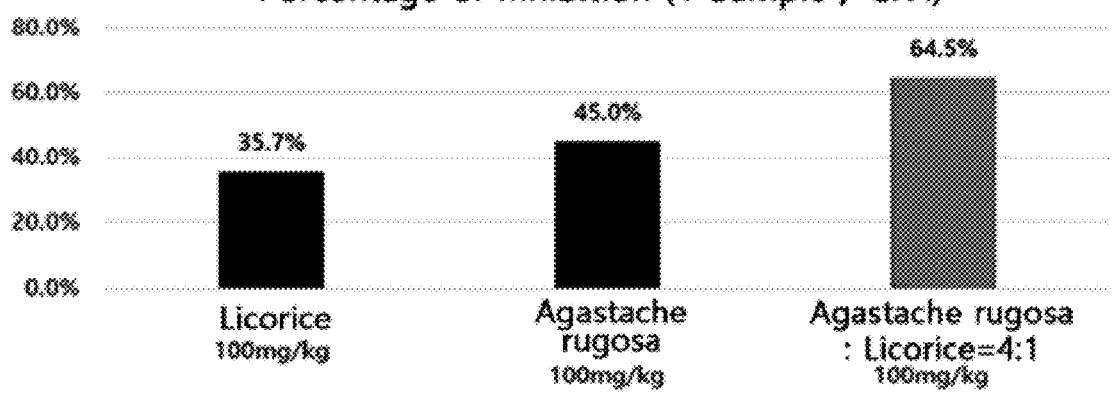
Figure 5:
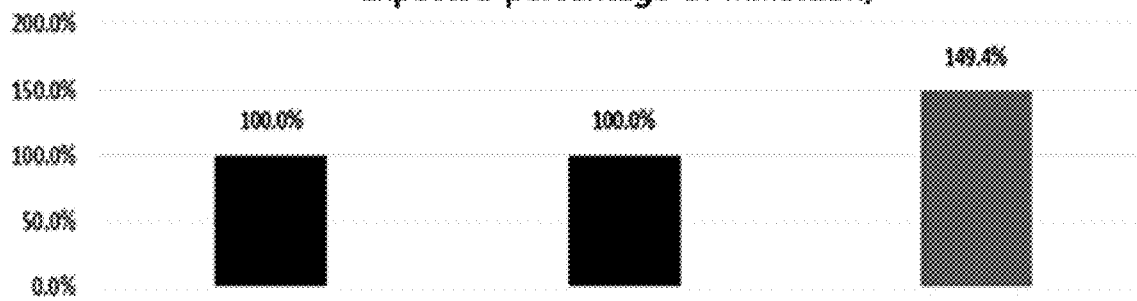

In still another specific embodiment of the present invention, as a result of confirming the MUC5AC mRNA expression levels in the lung tissue in order to confirm that sputum production was suppressed by the *Agastache rugosa* and licorice extract, it was confirmed that the inhibition of MUC5AC activity was high in the treatment groups of the *Agastache rugosa* and licorice complex extracts (Experimental Groups 1 to 3), compared to the *Agastache rugosa*-only extract (Comparative Example 1) and the licorice-only extract (Comparative Example 2) (FIG. 5).

Therefore, since the *Agastache rugosa* and licorice extract of the present invention can treat or ameliorate respiratory diseases through reducing cough through inhibition of TRPV1 activity; reducing lung inflammation through inhibition of CXCR1 or CXCR2 activity, or GR-1+CD11b+ cell ratio reduction; and suppressing sputum production through inhibition of MUC5AC activity, the *Agastache rugosa* and licorice extract of the present invention can be widely utilized in the prevention or treatment of respiratory diseases.

The pharmaceutical composition of the present invention may be formulated into various forms according to respective conventional methods. For example, it may be formulated into oral dosage forms such as powders, granules, tablets, capsules, suspensions, emulsions, syrups, and the like, and may be used in the form of external preparations, suppositories, and sterile injectable solutions. Depending on each formulation, pharmaceutically acceptable carriers, excipients, and diluents may be further included. In addition, it may be formulated and used in the form of external preparations such as powders, granules, tablets, capsules, suspensions, emulsions, syrups, aerosols, and the like, and sterile injectable solutions according to a conventional method.

Examples of the carriers, excipients, and diluents include lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil, and the like. When formulating the pharmaceutical composition or making a dosage form thereof, it is prepared using diluents or excipients such as fillers, extenders, binders, wetting agents, disintegrating agents, surfactants, and the like, which are generally used.

Solid preparations for oral administration include tablets, pills, powders, granules, capsules, and the like. These solid preparations are prepared by mixing at least one excipient in the composition, for example, starch, calcium carbonate, sucrose, lactose, gelatin, and the like. In addition, lubricants such as magnesium stearate talc are used in addition to simple excipients. Liquid preparations for oral use may include suspensions, intravenous solutions, emulsions, syrups, and the like, and in addition to water and liquid paraffin which are commonly used simple diluents, various excipients such as wetting agents, sweeteners, fragrances, preservatives, and the like may be included. Formulations for parenteral administration include sterilized aqueous solutions, non-aqueous solvents, suspensions, emulsions, lyophilized preparations, suppositories, and the like. As non-aqueous solvents and suspensions, propylene glycol, polyethylene glycol, vegetable oils such as olive oil, and injectable esters such as ethyl oleate may be used. As bases of suppositories, witepsol, macrogol, tween 61, cacao butter, laurin butter, glycerogelatin, and the like may be used.

As used herein, the term 'administration' means to provide the pharmaceutical composition of the present invention to a subject in any suitable way. The pharmaceutical composition of the present invention may be administered at an amount of an active ingredient or a pharmaceutical composition that induces a biological or medical response in a tissue system of an animal or a human, which is considered by researchers, veterinarians, doctors, or other clinicians, that is, at a clinically effective amount which is an amount that induces relief of symptoms of the disease or disorder to be treated. It is apparent to those skilled in the art that the therapeutically effective dose and the number of administrations with respect to the pharmaceutical composition of the present invention will vary depending on the desired effect. Therefore, the optimal dosage to be administered may be easily determined by those skilled in the art, and may be adjusted depending on the type of disease, the severity of the disease, the content of active ingredients and other ingredients contained in the composition, the type of formulation, the patient's age, weight, general health status, gender, and diet, administration time, routes of administration and secretion rates of the composition, treatment period, and various factors including drugs used concurrently. The pharmaceutical composition of the present invention may be administered at an amount of 1 mg/kg/day to 10,000 mg/kg/day, may be administered once a day, or may be divided and administered several times.

In still another aspect, the present invention relates to a health functional food composition for preventing or ameliorating a respiratory disease containing an *Agastache rugosa* and licorice extract as an active ingredient.

Since the *Agastache rugosa* and licorice extract of the present invention has efficacies of suppressing cough, suppressing lung inflammation through inhibiting the infiltration of neutrophils, and suppressing sputum, it may be used in a health functional food composition for preventing or ameliorating a respiratory disease, which is specifically as described above.

The formulation of the health functional food of the present invention may be in the form of powders, granules, pills, tablets, and capsules, as well as general foods or beverages.

The type of the food is not particularly limited, and examples of foods to which the substance may be added include meat, sausage, bread, chocolate, candy, snacks, confectionery, pizza, ramen, other noodles, gums, and dairy products including ice cream, various soups, beverages, teas, drinks, alcoholic beverages, vitamin complexes, and the like, and may contain all foods in the conventional meanings.

In general, when preparing a food or beverage, the composition may be added at an amount of 15 parts by weight or less, and preferably, 10 parts by weight or less, based on 100 parts by weight of the raw material. However, in the case of long-term intake for the purpose of health and hygiene or for the purpose of health control, the above amount may be the same or below the above range, and since the composition of the present invention has no problem in terms of safety, it may be used at an amount at or above the above range.

The beverage among the health functional foods according to the present invention may contain various flavoring agents, natural carbohydrates, or the like, as additional components as in a conventional beverage. The natural carbohydrates described above may be monosaccharides such as glucose and fructose, disaccharides such as maltose and sucrose, and polysaccharides such as dextrin and cyclodextrin, sugar alcohols such as xylitol, sorbitol, erythritol, and the like. As the sweetener, natural sweeteners such as thaumatin and a stevia extract, synthetic sweeteners such as saccharin and aspartame, and the like may be used. The ratio of the natural carbohydrate may be about 0.01 g to 0.04 g, and preferably, about 0.02 g to 0.03 g per 100 mL of the beverage according to the present invention.

In addition to the above, the health functional food according to the present invention may contain various nutrients, vitamins, electrolytes, flavoring agents, coloring agents, pectic acid and salts thereof, alginic acid and salts thereof, organic acids, protective colloidal thickeners, pH adjusting agents, stabilizers, preservatives, glycerin, alcohol, and carbonating agents used in carbonated beverages. In addition, the composition for preventing or ameliorating a respiratory disease according to the present invention may contain natural fruit juice, fruit juice drinks, and fruit flesh for the production of vegetable drinks. These ingredients may be used independently or in combination. The ratio of these additives is not limited, but is generally selected from the range of 0.01 to 0.1 parts by weight compared to 100 parts by weight of the health functional food of the present invention.

Hereinafter, preferred exemplary embodiments are provided to help understanding of the present invention. However, the following examples are only provided to understand the present invention more easily, and the contents of the present invention are not limited by the following examples.

Example 1: Preparation of *Agastache rugosa* Extract and Licorice Extract 1-1: Preparation of *Agastache rugosa* Extract (Comparative Example 1)

100 g of dried *Agastache rugosa* was added to 1.5 L of 30% ethanol and extracted at 70° C. for 4 hours. The extracted sample was filtered under reduced pressure with Whatman No. 2 filter paper, and the filtered extract was concentrated by a vacuum rotary concentrator and dried to prepare an *Agastache rugosa* extract.

1-2: Preparation of Licorice Extract (Comparative Example 2)

It was performed in the same manner as in Example 1, except that 100 g of dried licorice was used, and as a result, a licorice extract was prepared.

1-3. Preparation of *Agastache rugosa* and Licorice Extract (Weight Ratio of 1:1) (Experimental Example 1)

It was performed in the same manner as in Example 1, except that 50 g of dried *Agastache rugosa* and 50 g of dried licorice were used, and as a result, an *Agastache rugosa* and licorice extract (ratio of 1:1) was prepared.

1-4. Preparation of *Agastache rugosa* and Licorice Extract (Weight Ratio of 4:1) (Experimental Example 2)

It was performed in the same manner as in Example 1, except that 80 g of dried *Agastache rugosa* and 20 g of dried licorice were used, and as a result, an *Agastache rugosa* and licorice extract (ratio of 4:1) was prepared.

1-5. Preparation of *Agastache rugosa* and Licorice Extract (Weight Ratio of 6:1) (Experimental Example 3)

It was performed in the same manner as in Example 1, except that 86 g of dried *Agastache rugosa* and 14 g of dried licorice were used, and as a result, an *Agastache rugosa* and licorice extract (ratio of 6:1) was prepared.

Example 2: Confirmation of Cough Reducing Effect of *Agastache rugosa* and Licorice Extract In the present invention, the expression level of TRPV-1 known as a cough receptor was determined in order to confirm the cough-reducing efficacy of the *Agastache rugosa* and licorice extract.

First, MH-S cells which are alveolar macrophages were cultured in RPMI 1640 medium containing 10% FBS, 100 U/mL of penicillin, and 100 μg/mL of streptomycin at a condition of 37° C. and 5% $CO_2$. Cells were placed in a 6-well plate to be at $5 \times 10^5$ cells/mL, and a mixture (CFA) that was prepared by dissolving 50 mg/mL of coal and 50 mg/mL of fly ash in DMSO was treated at a concentration of 200 μg/mL to induce a reaction by fine dust for 1 hour. Afterwards, the *Agastache rugosa*-only extract (Comparative Example 1), the licorice-only extract (Comparative Example 2), and the *Agastache rugosa* and licorice extracts (Experimental Examples 1 to 3) prepared in Example 1 above were treated at a concentration of 60 μg/mL in a solution in which DMSO and PBS were mixed at 1:1 to culture for 6 hours at a condition of 37° C. and 5% $CO_2$, respectively.

After culturing for 6 hours, total RNA was isolated by treating a triazole (Ambion TRIzol® reagent; Grand Island, USA), and then cDNA was synthesized using a cDNA synthesis kit (ReverTraAce cDNA Synthesis kit; Toyobo, Japan). By using 100 ng of cDNA, qPCR was performed at a condition of 2 minutes at 50° C. 2 minutes at 95° C. 15 seconds at 95° C. for 40 repetitions, and 1 minute at 60° C. TaqMan-TRPV1 (Mm01246302_m1, FAM-MGB dye-labeled) and GAPDH (Mm99999915_g1, FAM-MGB dye-labeled) were purchased from Thermo Fisher Scientific to perform qPCR.

TABLE 1

Synergy effect according to mixing ratios of *Agastache rugosa* and licorice extracts
(TRPV1 inhibitory activity)

| Mixing ratio of *Agastache rugosa* and licorice | Mixing amount of *Agastache rugosa* (g) | Mixing amount of licorice (g) | Expected percentage of inhibition (expected efficacy) | Measured percentage of inhibition (actual efficacy) | Synergy (measured percentage of inhibition/expected percentage of inhibition) |
|---|---|---|---|---|---|
| 0:1 | 0 | 100 | 21.0% | 21.0% | 100.0% |
| 1:0 | 100 | 0 | 21.1% | 21.1% | 100.0% |
| 1:1 | 50 | 50 | 21.1% | 26.2% | 124.5% |
| 4:1 | 80 | 20 | 21.0% | 34.4% | 163.8% |
| 6:1 | 86 | 14 | 21.0% | 32.1% | 152.6% |

The expected percentage of inhibition for the *Agastache rugosa* and licorice extract was measured according to Mathematical Formula 1 below.

Expected percentage of inhibition (%)=[(measured percentage of inhibition of *Agastache rugosa*-only extract (%))×mixing amount of *Agastache rugosa* (g)/100]+[(measured percentage of inhibition of licorice-only extract (%))×mixing amount of licorice (g)/100]   [Mathematical Formula 1]

As a result, as shown in FIG. 1, it was confirmed that the TRPV1 activities were reduced in all the treatment groups of the *Agastache rugosa*-only extract, the licorice-only extract, and the *Agastache rugosa* and licorice extracts, compared to CFA treatment groups, and in particular, it was confirmed that the TRPV1 inhibitory activity was high in the *Agastache rugosa* and licorice extracts (Experimental Examples 1 to 3) compared to the treatment groups of the *Agastache rugosa*-only extract (Comparative Example 1) and the licorice-only extract (Comparative Example 2). This means that the *Agastache rugosa* and licorice extracts of the present invention reduce the activity of TRPV1 and thus, the effect of reducing cough by fine dust is excellent.

In addition, as shown in Table 1, it was confirmed that the TRPV1 inhibitory activity was increased depending on the mixing of the *Agastache rugosa* extract and the licorice extract, and in particular, it was confirmed that the TRPV1 inhibitory activity was most excellent when the *Agastache rugosa* and licorice extract was mixed at a weight ratio of 4:1.

Example 3: Confirmation of Inhibitory Effect of *Agastache rugosa* and Licorice Complex Extract on Lune Inflammation In the present invention, CXCR1 and CXCR2 expression levels were determined in order to confirm whether the *Agastache rugosa* and licorice complex extract inhibits lung inflammation.

First, MH-S cells which are alveolar macrophages were cultured in RPMI 1640 medium containing 10% FBS, 100 U/mL of penicillin, and 100 μg/mL of streptomycin at a condition of 37° C. and 5% $CO_2$. Cells were placed in a 6-well plate to be at $5\times10^5$ cells/mL, and a mixture (CFA) that was prepared by dissolving 50 mg/mL of coal and 50 mg/mL of fly ash in DMSO was treated at a concentration of 200 μg/mL to induce a reaction by fine dust for 1 hour. Afterwards, the *Agastache rugosa*-only extract (Comparative Example 1), the licorice-only extract (Comparative Example 2), and the *Agastache rugosa* and licorice complex extracts (Experimental Examples 1 to 3) prepared in Example 1 above were treated at a concentration of 60 μg/mL in a solution in which DMSO and PBS were mixed at 1:1 to culture for 6 hours at a condition of 37° C. and 5% $CO_2$, respectively.

After culturing for 6 hours, total RNA was isolated by treating a triazole (Ambion TRIzol® reagent; Grand Island, USA), and then cDNA was synthesized using a cDNA synthesis kit (ReverTraAce cDNA Synthesis kit; Toyobo, Japan). By using 100 ng of cDNA and primers of Table 2 below, qPCR was performed at conditions of 2 minutes at 50° C., 2 minutes at 95° C., 15 seconds at 95° C. for 40 repetitions, and 1 minute at 60° C.

TABLE 2

| Name of target gene | | Primer sequences (5' -> 3') | SEQ ID NO |
|---|---|---|---|
| CXCR1 | Forward direction | AATCTGTTGTGGCTTCACCCA | 1 |
| | Reverse direction | GCTATCTTCCGCCAGGCATAT | 2 |
| CXCR2 | Forward direction | AGCAAACACCTCTACTACCCTCTA | 3 |
| | Reverse direction | GGGCTGCATCAATTCAAATACCA | 4 |
| GAPDH | Forward direction | TGAAGCAGGCATCTGAGGG | 5 |
| | Reverse direction | CGAAGGTGGAAGAGTGGGAG | 6 |

TABLE 3

Inhibition of CXCR1 activity according to mixing ratios of
*Agastache rugosa* and licorice extracts

| Mixing ratio of *Agastache rugosa* and licorice | Mixing amount of *Agastache rugosa* (g) | Mixing amount of licorice (g) | Expected percentage of inhibition (expected efficacy) | Measured percentage of inhibition (actual efficacy) | Synergy (measured percentage of inhibition/expected percentage of inhibition) |
|---|---|---|---|---|---|
| 0:1 | 0 | 100 | 32.1% | 32.1% | 100.0% |
| 1:0 | 100 | 0 | 78.4% | 78.4% | 100.0% |
| 4:1 | 80 | 20 | 69.1% | 79.5% | 115.0% |

TABLE 4

Inhibition of CXCR2 activity according to mixing ratios of *Agastache rugosa* and licorice extracts

| Mixing ratio of *Agastache rugosa* and licorice | Mixing amount of *Agastache rugosa* (g) | Mixing amount of licorice (g) | Expected percentage of inhibition (expected efficacy) | Measured percentage of inhibition (actual efficacy) | Synergy (measured percentage of inhibition/expected percentage of inhibition) |
|---|---|---|---|---|---|
| 0:1 | 0 | 100 | −2.2% | −2.2% | 100.0% |
| 1:0 | 100 | 0 | 9.3% | 9.3% | 100.0% |
| 4:1 | 80 | 20 | 7.0% | 20.5% | 264.6% |

As a result, as shown in FIG. 2, FIG. 3, Table 3, and Table 4, it was confirmed that the CXCR1 and CXCR2 activities were reduced in all of the treatment groups of the *Agastache rugosa*-only extract, the licorice-only extract, and the complex extracts compared to CFA treatment groups, and in particular, it was confirmed that the CXCR1 and CXCR2 inhibitory activities were high in the treatment groups of the *Agastache rugosa* and licorice complex extracts (Experimental Examples 1 to 3) compared to the *Agastache rugosa*-only extract (Comparative Example 1) and the licorice-only extract (Comparative Example 2). This means that the *Agastache rugosa* and licorice complex extract of the present invention has an excellent effect of reducing inflammation in the lungs by lowering neutrophil chemotaxis through inhibitions of CXCR1 and CXCR2 activities.

Example 4: Confirmation of the Effect of Reducing Gr-1+CD11b+ Cell Ratio in the Lune Tissue by the *Agastache rugosa* and Licorice Complex Extract In the present invention, the Gr-1+CD11b cell ratio was determined in the lung tissue, in order to confirm whether the *Agastache rugosa* and licorice complex extract inhibits lung inflammation in vivo.

First, with 8 Balb/c male mice per group, in all groups excluding the normal group, a fine dust mixture (CFA) was prepared by mixing 10 mg/mL of coal, 10 mg/mL of fly ash, and 5 mg/mL of a diesel exhaust particle (DEP) mixture, which are components of fine dust, such that the final concentration of alum was 1%. The prepared fine dust mixture was directly injected into the airway and nose of the experimental animals by 100 μL each on day 3, day 6, and day 9 after the start of the experiment using the intranasal tracheal (INT) injection method.

Comparative Examples 1 and 2 and Experimental Examples 1 to 3 were diluted with a 0.5% sodium carboxymethyl cellulose (CMC, 419273. Sigma-Aldrich) solution at a concentration of 100 mg/kg and was orally administered every day for 11 days. On day 12 after the start of the experiment, autopsy was performed to analyze lung tissue.

A specific fluorescence fluorescent antibody staining method was performed using a CD11b antibody (553310, BD Biosciences, USA) and a Gr-1 antibody (553128, BD Biosciences, USA) with a fluorescent label bound to the lung tissue, and fluorescence-activated cell sorting (FACS, BD Biosciences, USA) was used to measure the ratio of leukocytes (CD11b+/Gr-1+ leukocyte) expressing CD11b and Gr-1 among the total leukocytes.

TABLE 5

Inhibitory activity of CD11b+/Gr-1+ cell ratios according to the mixing ratios of Agastache rugosa and licorice extracts

| Mixing ratio of Agastache rugosa and licorice | Mixing amount of Agastache rugosa (g) | Mixing amount of licorice (g) | Expected percentage of inhibition (expected efficacy) | Measured percentage of inhibition (actual efficacy) | Synergy (measured percentage of inhibition/expected percentage of inhibition) |
|---|---|---|---|---|---|
| 0:1 | 0 | 100 | 20.6% | 20.6% | 100.0% |
| 1:0 | 100 | 0 | 17.4% | 17.4% | 100.0% |
| 4:1 | 80 | 20 | 19.96% | 42.9% | 237.7% |

As a result, as shown in FIG. 4 and Table 5, it was confirmed that the ratios of CD11b+/Gr-1+ leukocytes were reduced in all of the treatment groups of the *Agastache rugosa*-only extract, the licorice-only extract and the complex extracts compared to CFA treatment groups, and in particular, it was confirmed that lower CD11b+Gr-1+ leukocyte ratios were exhibited in the treatment groups of the *Agastache rugosa* and licorice complex extracts (Experimental Examples 1 to 3) compared to the *Agastache rugosa*-only extract (Comparative Example 1) and the licorice-only extract (Comparative Example 2). That is, it was confirmed that the *Agastache rugosa* and licorice complex extract showed remarkable inhibitory activity for bronchial inflammation.

Example 5: Confirmation of the Effect of Suppressing Sputum Production by the *Agastache rugosa* and Licorice Complex Extract In the present invention, the MUC5AC mRNA expression levels were determined in the lung tissue, in order to confirm whether sputum production was suppressed by the *Agastache rugosa* and licorice complex extract.

First, 500 mL of RNAzolB (Tel-Test, Friendswood, USA) was added to the lung tissue extracted in Example 4 above and pulverized until dissolved. After adding 50 mL of $CHCl_3$ to the mixed suspension, it was mixed again for 15 seconds. It was left on ice for 15 minutes and centrifuged at 13,000 rpm. About 200 mL of the supernatant was recovered and the same amount of 2-propanol (I9516, Sigma-Aldrich, USA) was mixed, slowly shaken, and left on ice for 15 minutes. It was centrifuged again at 13,000 rpm, washed with 80% ethanol, and dried in vacuum for 3 minutes to extract RNA. The extracted RNA was dissolved in 20 mL of distilled water treated with diethyl pyrocarbonate (DEPC, 750023, Thermo Scientific, USA), inactivated at 75° C., and used for cDNA synthesis.

2 μg of the prepared total RNA was placed in 2 U/tubeDNase I (AB0620, Thermo Scientific, USA) to react at 37° C. for 30 minutes, and then denatured at 75° C. for 10 minutes. After adding 2.5 mL of 10 mM dNTPs mix (4030, TaKaRa, Japan), 1 mL of random sequence hexanucleotides (N8080127, Thermo Scientific, USA), 1 mL of RNase inhibitor (2313A, TaKaRa, Japan), 1 mL of 100 mM DTT (4029, TaKaRa. Japan), and 4.5 mL of 5×RTbuffer (M5313, Promega, USA), 4.5 mL of M-MLV RT (M1701, Promega, USA) were added again, and the final volume was adjusted to 20 mL by DEPC-treated distilled water. After mixing well, the mixture was centrifuged at 2,000 rpm for 5 seconds and reacted for 60 minutes in a 37° C. heating block (Multi-blok heater, TRIPUNITHURA, USA) to synthesize cDNA. Then, it was left at 95° C. for 5 minutes, and synthesized cDNA was used for PCR by inactivating M-MLV RT. Sper-Taqman PCR Master mix (4304437, Applied Biosystems, USA) was used, and it was reacted such that the final concentration of the primer (refer to Table 6) was 200 nM. For the conditions of RT-PCR, predenaturation was performed at 50° C. for 2 minutes, 94° C. for 10 minutes, and 95° C. for 0.15 minutes for 40 cycles, and 60° C. for 1 minute. GAPDH (4352339E, Thermo Scientific, USA) was used as the internal standard.

TABLE 6

| Name of target gene | Primer | sequences (5' -> 3') | SEQ ID NO |
|---|---|---|---|
| MUC5AC | Forward direction | AGAATATCTTTCAGGACCCCTGCT | 7 |
|  | Reverse direction | ACACCAGTGCTGAGCATACTTTT | 8 |
| GAPDH-VIC | Probe | CATGTTCCAGTATGACTCCACTCACG | 9 |

TABLE 7

Inhibition of MUC5AC activity according to the mixing ratios of Agastache rugosa and licorice extracts

| Mixing ratio of Agastache rugosa and licorice | Mixing amount of Agastache rugosa (g) | Mixing amount of licorice (g) | Expected percentage of inhibition (expected efficacy) | Measured percentage of inhibition (actual efficacy) | Synergy (measured percentage of inhibition/ expected percentage of inhibition) |
|---|---|---|---|---|---|
| 0:1 | 0 | 100% | 35.7% | 35.7% | 100.0% |
| 1:0 | 100 | 0 | 45.0% | 45.0% | 100.0% |
| 4:1 | 80 | 20% | 41.9% | 64.5% | 149.4% |

As a result, as shown in FIG. 5 and Table 7, it was confirmed that the expression levels of MUC5AC gene were reduced in all of the treatment groups of the *Agastache rugosa*-only extract, the licorice-only extract, and the complex extracts compared to CFA treatment groups, and in particular, it was confirmed that the MUC5AC inhibitory activities were higher in the treatment groups of the *Agastache rugosa* and licorice complex extracts (Experimental Examples 1 to 3) compared to the *Agastache rugosa*-only extract (Comparative Example 1) and the licorice-only extract (Comparative Example 2). That is, it was confirmed that the *Agastache rugosa* and licorice complex extract suppressed sputum production.

INDUSTRIAL APPLICABILITY

The *Agastache rugosa* and licorice extract of the present invention has the efficacies of reducing cough, reducing lung inflammation, and suppressing sputum production, and in particular, since it is confirmed that the efficacy of the *Agastache rugosa* and licorice complex mixture is maximized at a specific mixing ratio, it can be widely utilized as a composition for the prevention or treatment of respiratory diseases caused by fine dust.

The invention claimed is:

1. A method for preventing, ameliorating or treating a respiratory disease, comprising administering a composition consisting of an *Agastache rugosa* extract and a licorice extract to a subject in need thereof at an effective amount, wherein the respiratory disease is induced by inhalation of fine dust and is one or more selected from the group consisting of respiratory inflammatory pulmonary disease, chronic obstructive pulmonary disease (COPD), sinusitis, allergic rhinitis, lower respiratory tract infection, acute and chronic bronchitis, emphysema, pneumonia, bronchial asthma, bronchiectasis, emphysema, pulmonary tuberculosis sequelae, acute respiratory distress syndrome, and pulmonary fibrosis.

2. The method of claim 1, wherein the *Agastache rugosa* extract and the licorice extract are mixed with *Agastache rugosa* and licorice at a weight ratio of 1:1 to 6:1.

3. The method of claim 1, wherein the *Agastache rugosa* extract and the licorice extract reduce cough through inhibition of TRPV1 activity, reduce lung inflammation through inhibition of CXCR1 or CXCR2 activity, or GR-1+CD11b+ cell ratio reduction, and suppress sputum production through inhibition of MUC5AC activity.

* * * * *